United States Patent [19]
Smith et al.

[11] Patent Number: 5,543,318
[45] Date of Patent: Aug. 6, 1996

[54] METHOD OF ISOLATION, CULTURE AND PROLIFERATION OF HUMAN ATRIAL MYOCYTES

[76] Inventors: David A. Smith, 3244 Belle Ct., Royal Oak, Mich. 48073; Laurace E. Townsend, 868 Whittier, Grosse Pointe Park, Mich. 48230

[21] Appl. No.: 531,793

[22] Filed: Sep. 21, 1995

Related U.S. Application Data

[63] Continuation of Ser. No. 236,689, Apr. 29, 1994, abandoned, which is a continuation of Ser. No. 742,613, Aug. 8, 1991, abandoned, which is a continuation-in-part of Ser. No. 713,949, Jun. 12, 1991, abandoned.

[51] Int. Cl.$^6$ ................................................ C12N 5/00
[52] U.S. Cl. ................................ 435/240.2; 435/240.1; 435/240.21; 435/240.23
[58] Field of Search .......................... 435/240.1, 240.2, 435/240.21, 240.23, 240.243, 240.3, 240.31

[56] References Cited

U.S. PATENT DOCUMENTS

| | | | |
|---|---|---|---|
| 4,350,687 | 9/1982 | Lipton et al. | 424/177 |
| 4,479,896 | 10/1984 | Antoniades | 260/112 |
| 4,590,003 | 5/1986 | Twardzik et al. | 530/330 |
| 4,645,828 | 2/1987 | Twardzik et al. | 530/324 |

OTHER PUBLICATIONS

Bashor, Methods in Enzymology, vol. LVIII, published in 1979, pp. 129–130.
Kardami, Molecular & Cellular Biochemistry, 92:129–135 (1990).
William C. Claycomb, et al., "Culture and Characterization of Fetal Human Atrial and Ventricular Cardiac Muscle Cells," *In Vitro Cell. Dev. Biol.* 25:1114–1120 (1989).
D. Stave Kohtz, et al., "Growth and Partial Differentiation of Presumptive Human Cardiac Myoblasts in Culture," *J. Cell Biol.* 108:1067–1078 (1989).
Peter Libby, "Long–Term Culture of Contractile Mammalian Heart Cells in a Defined Serum–Free Medium that Limits Non–Muscle Cell Proliferation," *J. Mol. Cell. Cardiol.* 16:803–811 (1984).
C. J. S. Hassall, et al., "Immunocytochemical Studies of Cardiac Myocytes and Other Non–Neuronal Cells of the Fetal Human Heart in Culture," *Anat. Embryol.* 182:339–346 (1990).
Marc Cantin et al., "DNA Synthesis in Cultured Adult Cardiocytes," *Science* 214:569–570 (1981).
S. P. Halbert, et al., "Growth of Dissociated Beating Human Heart Cells in Tissue Culture," *Life Sciences* 13:969–975 (1973).
S. L. Jacobson, et al., "Long–Term Primary Cultures of Adult Human and Rat Cardiomyocytes," *Basic Res. Cardiol.* 80, Suppl. 1:79–82 (1985).

A. C. Nag, et al., "Adult Cardiac Muscle Cells in Long––Term Serum–Free Culture: Myofibrillar—Organization and Expression of Myosin Heavy Chain Isoforms," *In Vitro Cell. Dev. Biol.* 26:464–470 (1990).
A. C. Nag, et al., "Long–Term Cell Culture of Adult Mammalian Cardiac Myocytes: Electron Microscopic and Immunofluorescent Analyses of Myofibrillar Structure," *J. Mol. Cell. Cardiol.* 15:301–317 (1983).
A. C. Nag, et al., "Factors Controlling Embryonic Heart Cell Proliferation in Serum–Free Synthetic Media," *In Vitro Cell. & Dev. Bio.* 21:553–562 (1985).
Takahiko Suzuki, et al. "Serum–Free, Chemically Defined Medium to Evaluate the Direct Effects of Growth Factors and Inhibitors on Proliferation and Function of Neonatal Rat Cardiac Muscle Cells in Culture," *In Vitro Cell. & Dev. Biol.*, 25:601–606 (1989).
Iris S. Pollinger, "Separation of Cell Types in Embryonic Heart Cell Cultures," *Exptl. Cell Res.* 63:78–82 (1970).
J. Wharton, et al., "Immunohistochemical and ultrastructural localisation of Peptide–Containing Nerves and Myocardial Cells in the Human Atrial Appendage," *Cell Tissue Res.* 254:155–166 (1988).
Patrice Bouvagnet, et al., "Developmental Changes in the Human Cardiac Isomyosin (1987). Distribution: An Immunohistochemical Study Using Monoclonal Antibodies," *Circ. Res.* 61:329–355 (1987).
Alan W. Everett, "Isomyosin Expression in Human Heart in Early Pre– and Post–Natal Life," *Mol. Cell Cardiol.* 18:607–615 (1986).
Melvyn Lieberman, et al, "The Cultured Heart Cell: Problems and Prospects," *Meth. Cell Biol.*, 21A, Chapter 12, 187–203 (1980).
"Clues to cardiac cell growth from a big–hearted mouse," *AHA Cardiovascular Research Report.* No. 35:6 (Summer 1990).
Kardami, E., "Stimulation and Inhibition of Cardiac Myocyte Proliferation *In Vitro*," *Mol. Cell. Biochem.* 92:129–135 (1990).

*Primary Examiner*—Michael G. Wityshyn
*Assistant Examiner*—Susan M. Dadio
*Attorney, Agent, or Firm*—Harness, Dickey & Pierce, P.L.C.

[57] ABSTRACT

The present invention provides methods for isolating and culturing human myocardiocytes from adult human atrial tissue and proliferating cultures resulting therefrom. In one embodiment, the myocardial cells are substantially dissociated through sequential enzymatic digestion and plated on growth medium selective for myocardial cell growth. In another embodiment, the atrial tissue is subjected to only limited digestion to provide an explant tissue portion which is cultured under conditions favoring cell proliferation. Cells migrating from the explant are isolated and subjected to time-based selective attachment and selective growth techniques which result in a myocardial cell culture of approximately 93% purity.

23 Claims, 10 Drawing Sheets

METHOD OF ISOLATION, CULTURE AND PROLIFERATION OF HUMAN ATRIAL MYOCYTES

This is a continuation of U.S. application Ser. No. 08/236,689, filed Apr. 29, 1994, now abandoned, which is a continuation of U.S. application Ser. No. 07/742,613, filed Aug. 8, 1991, now abandoned, which is a continuation-in-part of U.S. application Ser. No. 07/713,949, filed Jun. 12, 1991, now abandoned.

FIELD OF THE INVENTION

BACKGROUND OF THE INVENTION

Atrial myocytes represent a heterogeneous population of cells. The common atrial myocyte is specialized not only as a contractile muscle cell but also as an endocrine cell secreting atrial natriuretic peptide (ANP) which has potent diuretic and hypotensive effects and inhibits renin and aldosterone secretion. DeBold, A. *J. Science* 230:767 (1985). Atrial myocytes thus have the machinery responsible for synthesis, processing and releasing ANP, including rough endoplasmic reticulum, free ribosomes, Golgi apparatus and atrial specific granules. Other ultrastructural details unique to atrial myocytes include absent or few transverse tubules and tremendous variation in the organization of sarcomeres, from dense and well-organized, as seen in ventricular cells, to scanty and haphazard. See Severs, N.J. *Isolated adult cardiomyocytes.* Piper et al. (ed.) *Constituent cells of the heart and isolated cell models in cardiovascular research. Structure and metabolism.* Vol. 1 Boca Raton: CRC Press, pp. 16–18 (1989). The ultrastructural characteristics of atrial myocytes, as well as their neurosecretory potential and their response to in vivo injury, differ so greatly from their ventricular and skeletal muscle counterparts, that they can be considered a different class of striated muscle cells. Techniques for culturing myocardiocytes from rats, chick, guinea pigs and cats have been established and are routinely used for cardiac muscle research. See Harary, I. et al., *Exp. Cell. Res.* 29:451–456 (1963); Friedman, B. J. et al., *J. Nucl. Med.* 28(9):1453–1460 (1987); Nakajima, T. et al., *Circ. Res.* 64(2):297–303 (1989); Follmer, C. H. et al., *J. Physiol.* 384:169–197 (1987), respectively. For example, the long term culture of adult rat myocardiocytes, which exhibit morphologic changes reminiscent of embryonic or neonatal cardiac muscle cells, has been described. Nag, A. C. et al., *J. Mol. Cell. Cardiol.* 15:301–317 (1983); see also Schwartzfeld, J. A. et al., *J. Mol. Cell Cardiol.* 13:563–575 (1981); Claycomb, W. C., *J. Cell. Biol.* 91:342 (1981); Cantin, M. et al., *Science* 214:566–579 (1981); Libby, P., *J. Mol. Cell. Cardiol* 16:803–811 (1984). Methods for culturing human fetal and transformed myocardial cells have also been developed. Holtz, D. S. et al., *J. Cell. Biol.* 108:1067–1078 (1989); Hassail, C. J. S. et al., *Anat. Embryol* 182:339–346 (1990); Claycomb, E. C. et al., In Vitro *Cell. Dev. Biol.* 25:1114–1120 (1989); Wang, Y. C. In Vitro *Cell. Dev. Biol.* 27A:63–74 (1991). The successful culture of human adult myocardiocytes derived from either the atrium or ventricle has not, however, been reported. See Cardiovasc. Res. No. 35, Summer 1990 (p. 6), American Heart Association.

Since human adult tissue is of great interest due to numerous disease states, it would be desirable to provide techniques for the isolation, culture and proliferation of adult human myocardiocytes for research and clinical applications.

SUMMARY OF THE INVENTION

The present invention provides a method of isolating and culturing human myocardiocytes generally comprising the steps of providing a sample of human atrial tissue and selecting for myocardiocytes in the sample. The present invention further provides proliferating human myocardiocyte cultures produced by the methods of the invention.

In one embodiment of the present invention, the cells in the atrial tissue sample are substantially disassociated through sequential enzymatic digestion and selection is accomplished using selective growth medium. In another embodiment, atrial explant tissue is cultured and myocardiocyte progeny thereof are selected through time-based selective attachment.

The methods and cultures of the invention provide a research and analytical tool uniquely suited for growth factor and metabolic studies, for determining the effect of age, disease states and growth factors on myocardial mitotic ability, and for other cardiac studies. The monitoring of treatment, testing and diagnosis of cardiac conditions and pharmaceutical screening utilizing the present methods and cultures of the invention are also contemplated as falling within its scope. The methods of the invention further provide means for the expansion of myocardial cells in culture for production of ANP and other myocardiocyte products or for implantation in diseased, inadequate or infarcted myocardium.

Other features and advantages of the present invention will be become apparent from the following description and appended claims, taken in conjunction with the accompanying drawings.

BRIEF DESCRIPTION OF THE DRAWINGS

FIG. 8 is a scattergram of the myocardial tissue samples described in Table 1 separated according to growth characteristics and plotted by age of tissue donor. Average age of cells which grew was 43.8±7.2; average age of cells which did not grow was 62/7±11. p=0.0095.

DETAILED DESCRIPTION OF THE PREFERRED EMBODIMENTS

The cells in the Specific Examples below were harvested from adult human myocardial tissue with ischemic pathology, tissue that is of particular interest for identifying human growth factors that can prevent or partially reverse damage to the heart. By adult myocardial tissue is meant tissue comprising myocardial cells which are predominately terminally differentiated. It will be appreciated, however, that the methods of culture of the present invention are applicable to both differentiated and nondifferentiated human tissues, and are also applicable to healthy myocardial tissue.

In one preferred embodiment of the invention, detailed in Specific Example 1, the atrial tissue was minced and sequentially digested with collagenase for two to nine hours. The single cell suspension was initially cultured in serum containing growth medium, then transferred to defined MCDB 107 medium selective for myocardial growth. Suzuki, T. et al., In Vitro Cell. Dev. Bio. 25:601–606 (1989). Resulting cultures comprised nearly 43% myocardial cells. In another preferred embodiment, described in Specific Example 2, the atrial tissue was minced and subjected to limited collagenase digestion, resulting in a tissue explant and dissociated cells. The tissue explant was cultured and cells migrating from the explant isolated. The isolated cells were then subjected to myocardiocyte selection using time-based selection attachment with cells not attaching within about 30 minutes being discarded. Attached cells were further selected through culture in MCDB 107. The explant culture method resulted in a highly pure culture of approximately 93% myocardiocytes.

Identification of myocardial cells was accomplished using antibodies specific for muscle myosin, myoglobin, and atrial natriuretic peptide (ANP). Immunoperoxidase stains were consistent with cells of cardiac muscle origin, while control fibroblasts did not reflect the same findings. Repeat stains on the same harvest and stains performed on additional harvests verified these findings. Transmission electron microscopy (TEM) was also performed to confirm the myocardial origin of the cells. Ultrastructural organization was consistent with myocardiocytes undergoing myofibrillar reorganization. The above results evidence the successful culture of adult human atrial myocytes, even though organized sarcomeres and t-tubules were absent at this stage of myofibrillar reorganization.

Using the culture techniques of the present invention, human adult myocardiocytes were cultured for up to seven passages.

SPECIFIC EXAMPLES

SPECIFIC EXAMPLE 1.

Dissociation Method
MATERIALS AND METHODS
Cell harvest

Atrial tissue was obtained from right atrial appendages harvested from cardiovascular surgery patients undergoing procedures requiring heart-lung bypasses. The patients were randomly selected and included both sexes, with ages ranging from 38 to 81 years old. The appendages are removed routinely in order to insert the venous bypass cannulae into the right atria. The appendages used in this example were obtained immediately after removal and placed in ice-saline slush. After rinsing in saline, the tough epicardial covering was removed using a scalpel to reduce the amount of connective tissue included in the cell harvest. The remaining "pure" atrial muscle was minced into small (0.5–1.0 mm$^3$) pieces and placed in cold Hank's Balanced Salt Solution (HBSS) without calcium or magnesium (Whittaker, Walkerville, Mass.). The atrial pieces were then transported from the operating suite to the tissue culture laboratory.

Digestion and plating

The minced atrial tissue was digested in 0.14% collagenase solution (Worthington, Freehold, N.J.) at a concentration of 1.43 mg/ml. The pieces were placed in 35 ml of this solution and digested in a shaker at 37° C. at 125 RPM for one hour. The supernatant was removed from the atrial tissue and centrifuged at 3500 RPM for 10 minutes at 37° C. Another 35 ml of collagenase solution was placed with the minced tissue while the supernatant was spinning and the digestion continued for another hour. The cell suspension formed a pellet during centrifugation. The supernatant collagenase solution was removed and set aside for use in the third digestion. The cell pellet was resuspended in 2 ml of Eagle's Minimal Essential Medium (EMEM) with Earle's Salts (Whittaker) containing 30% newborn calf serum (Whittaker) and 0.1% antibiotic solution-10,000 units/cc Penicillin G, 10,000 μg/cc Streptomycin and 25 μg/cc Amphotericin B (Gibco, Grand Island, N.Y.). This process was continued for a total of eight digestions.

The first pellet was discarded and digestions 2–8 pooled. The cell concentration was checked using a hemacytometer and adjusted to 1×10$^5$ cells/ml with EMEM. The cells were plated on 35 mm gelatin coated dishes (Corning, Corning, N.Y.) and incubated at 37° C. in 5% CO$_2$ atmosphere. Medium was changed every three days for the first two weeks of growth, then every five to seven days thereafter.

When the cultures spread out and approached confluence, they were treated with trypsin and transferred to 60 mm gelatin coated dishes (Corning) in EMEM. As the cultures again spread out and approached confluence, they were treated with trypsin and transferred to T-75 flasks (Corning) in MCDB 107 (Sigma, Saint Louis, Mo.).

Immunoperoxidase staining

A portion of the cells grown in MCDB 107 were plated on four chamber gelatin coated slide culture plates (Lab Tek, Naperville, Ill.). Control cells were human umbilical endothelial cell and human skin fibroblast cultures (Beaumont Research Institute, Royal Oak, Mich.) that were grown in M199 with 20% fetal bovine serum, 1% L-glutamine, 0.1% of 5 mg/ml insulin-5 mg/ml transferrin-5 µg/ml selenious acid (Collaborative Research Inc.), 0.6 ml heparin (0.015% in M199), 0.1% antibiotic-antimycotic solution (Gibco Laboratories: 10,000 units/ml sodium pennicilin G, 100,000 mcg/ml streptomycin sulfate and 25 mcg/ml amphotericin B), and 300 µg/ml of Endothelial Cell Growth Supplement (ECGS) from Biotechnology Research Inst., Rockville, Md. When control cultures and harvested cells spread out and approached confluence they were rinsed with HBSS and fixed with 10% formalin for 10 minutes. The chambers were removed and the cells remaining on the plates were stained with immunoperoxidase stains for smooth muscle α-actin (Lipshaw, Detroit, Mich.), striated muscle specific myosin (Sigma, St. Louis, Mo.), myoglobin (Dako, Carpinteria, Calif.), factor VIII (Lipshaw, Detroit, Mich.), and atrial natriuretic factor peptide (Research and Diagnostic Antibodies, Berkeley, Calif.) The plates were then examined using light microscopy.

Electron microscopy

A portion of cells growing in MCDB 107 were plated on 96-well gelatin-coated plates (Corning). When they spread out and approached confluence they were rinsed with HBSS and fixed with 2.5% glutaraldehyde, 0.2M cacodyiate buffer, pH 7.4 (Polysciences, Inc., Warrington, Pa.), post-fixed with 1% osmium tetroxide (Polysciences, Inc.), embedded in Epon LX-112 resin (Ladd's Research, Burlington, Va.), stained with 0.03% lead citrate (Eastman Kodak, Rochester, N.Y.) and saturated uranyl acetate (Pelco Co., Tustin, Calif.) in 50% ethyl alcohol and then examined under transmission electron microscopy.

RESULTS

Cell attachment and morphology

Figure 1:
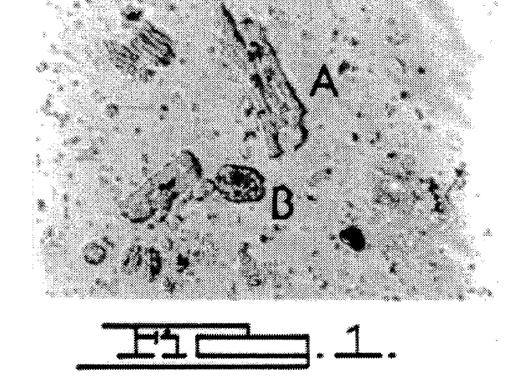
FIG. 1 a photomicrograph (×250) of harvested atrial cells settled on the bottom of the culture plate at 24 hours: A) myocardiocyte; and B) nonmyocardiocyte.

Suspended cells settled very quickly. Usually within one hour after plating, the majority of harvested cells were seen on the bottom of the culture dish. The cells were not adherent, however, as gentle agitation resuspended them. The cells required approximately 48–72 hours after plating before attachment and cytoplasmic spreading occurred. The settled cells were inspected using phase-contrast microscopy and categorized as myocardial or nonmyocardial on the basis of their appearance. As shown in the photomicrograph of FIG. 1, myocardial cells were rectangular or spindle-shaped, and had cross striations, a single nucleus with prominent nucleolus and occasional branching. Nonmyocardial cells were round or oval shape and lacked clearly identifiable cross striations. The cells were 42.8% myocardial and 57.2% nonmyocardial as determined morphologically.

Cell yields

Figure 2:
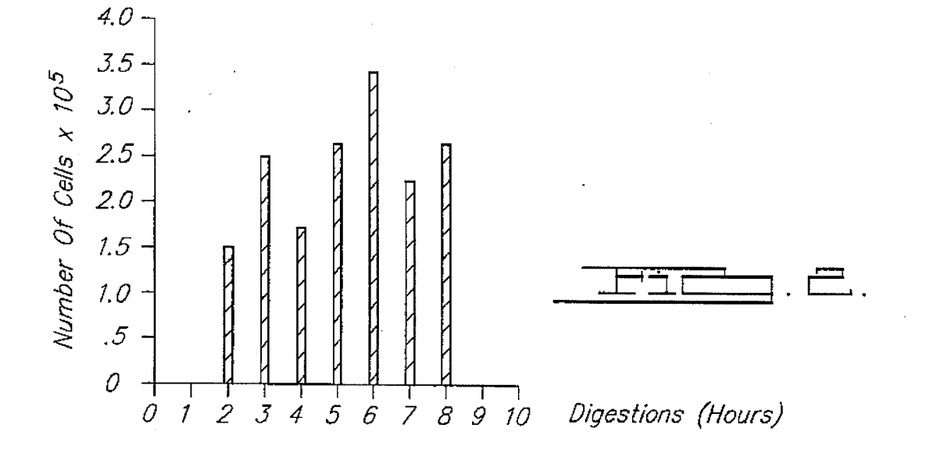
FIG. 2 is a bar graph illustrating cell yield versus time of digestion, with hemacytometric cell counts taken at the time of harvest for each digestion.
Figure 3:
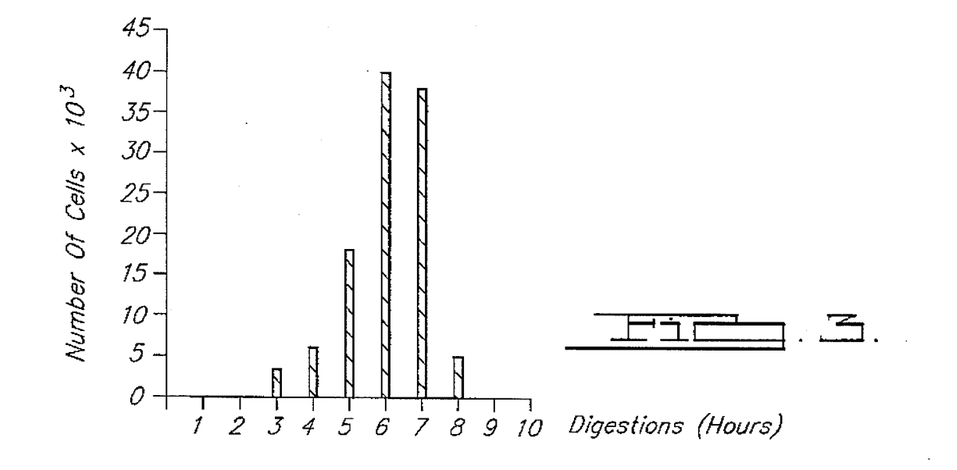
FIG. 3 is a bar graph illustrating cell viability verus time of digestion, with planimetric cell counts taken at one week for each digestion.

Cell yields, including both myocardial and nonmyocardial cells, were relatively constant for digestions 2–8 as illustrated by the bar graph of FIG. 2. Cell counts ranged from $1.5 \times 10^5$/ml at two hours to $3.4 \times 10^5$/ml at six hours. Cell viability, however, varied with the length of digestion. Referring now to the bar graph of FIG. 3, planimetric cell counts measured at one week for cultures plated separately for each digestion showed a steady increase in cell viability in digestions one through seven, peaking at six to seven hours then dropping abruptly after that, so that viability was nil at nine hours or more of digestion.

Growth characteristics

Figure 4:
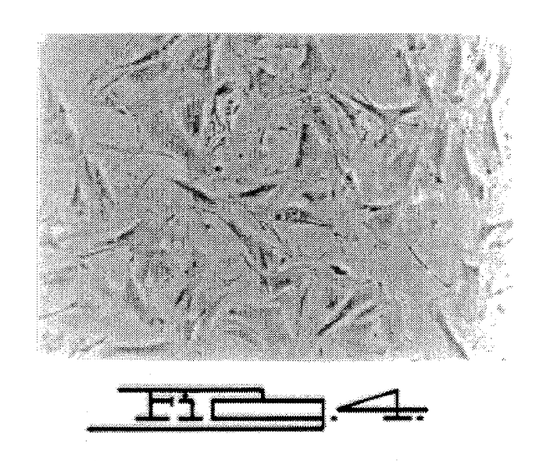
FIG. 4 is a photomicrograph (×50) of cells cultured in EMEM nearing confluence, immediately before passage.
Figure 5:
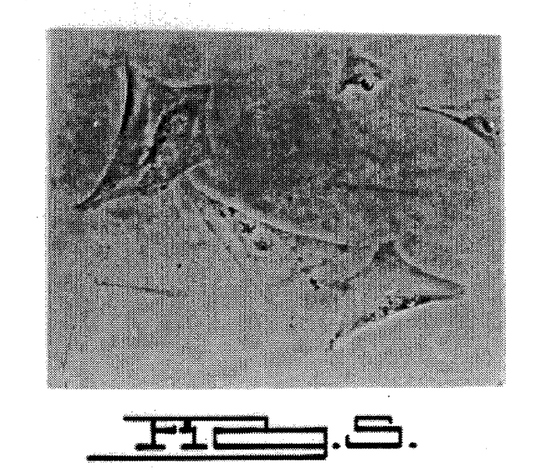
FIG. 5 is a photomicrograph (×125) of cells cultured in MCDB 107 with characteristic "bat-winged" morphology.
Figure 6A:
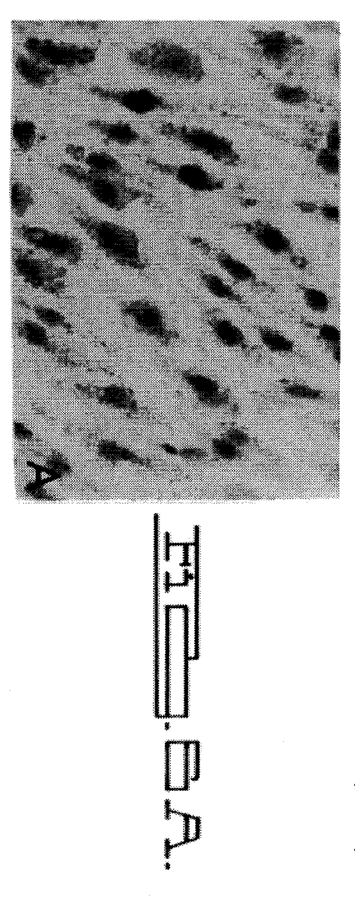
FIG. 6 is a photomicrograph (×500) demonstrating immunoperoxidase staining characteristics of presumptive myocardiocytes, control fibroblasts and control endothelial cells: A) endothelial cells with cytoplasmic granules staining for Factor VIII; B) myocardiocytes with no Factor VIII staining; C) fibroblasts with no staining for myoglobin; D) myocardiocytes with diffuse cytoplasmic staining for myoglobin; E) fibroblasts with no significant actin filament staining; and F) myocardiocytes with actin filament staining.
Figure 6B:
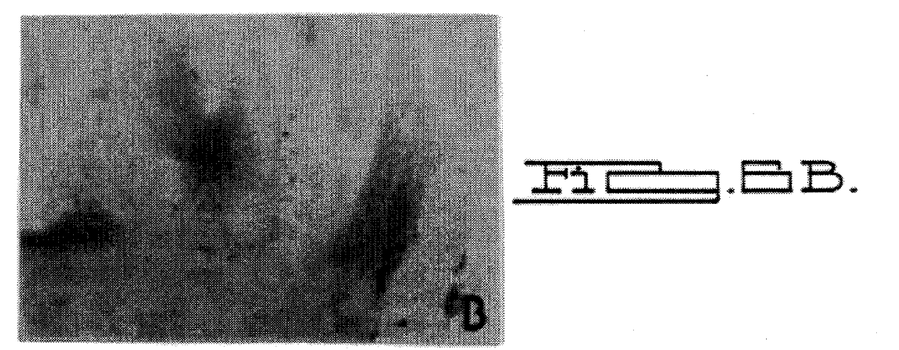
Figure 6C:
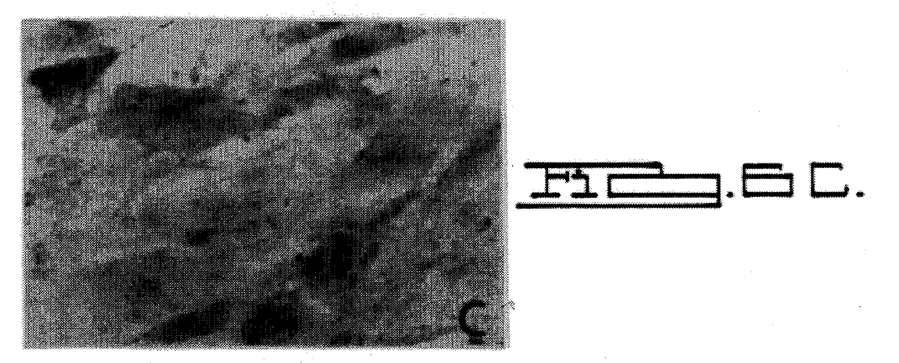
Figure 6D:
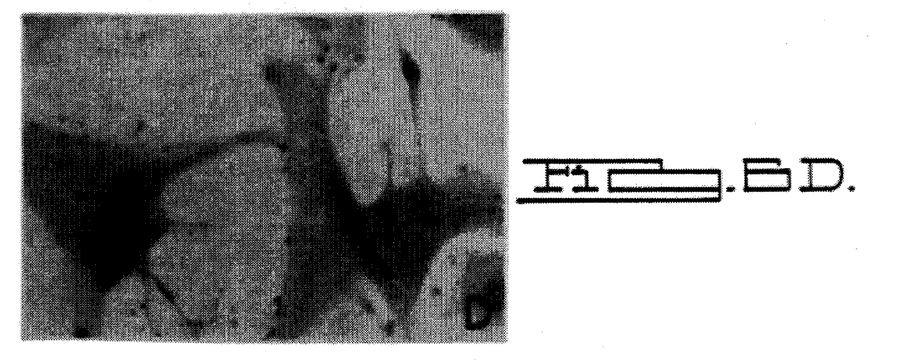
Figure 6E:
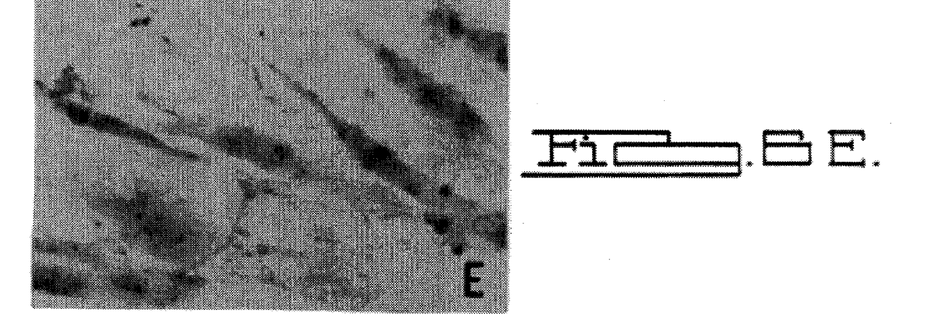
Figure 6F:
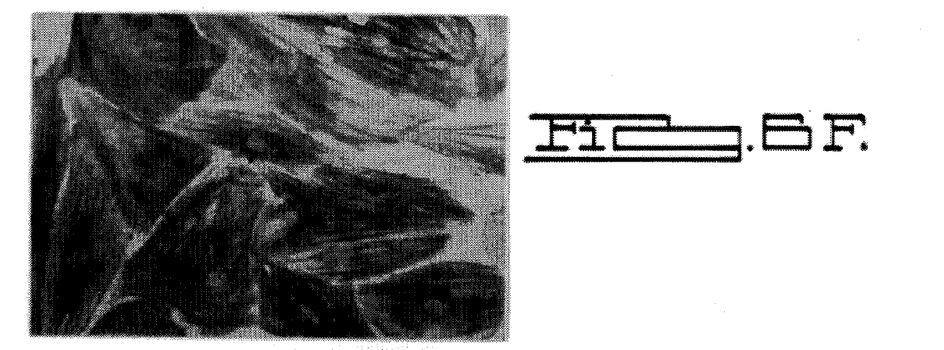
Figure 6G:
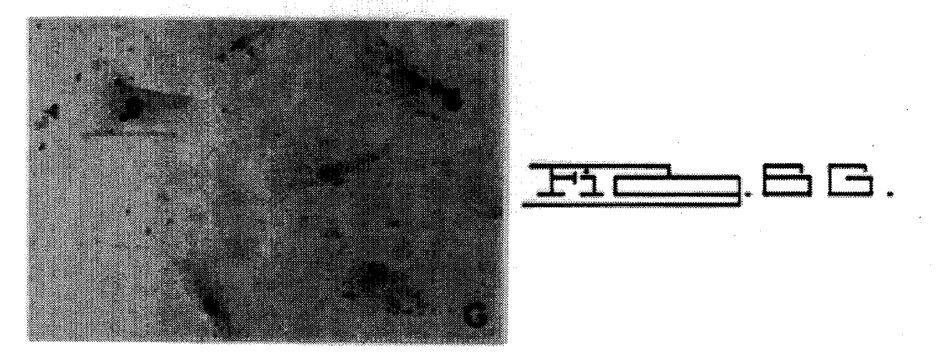
Figure 6H:
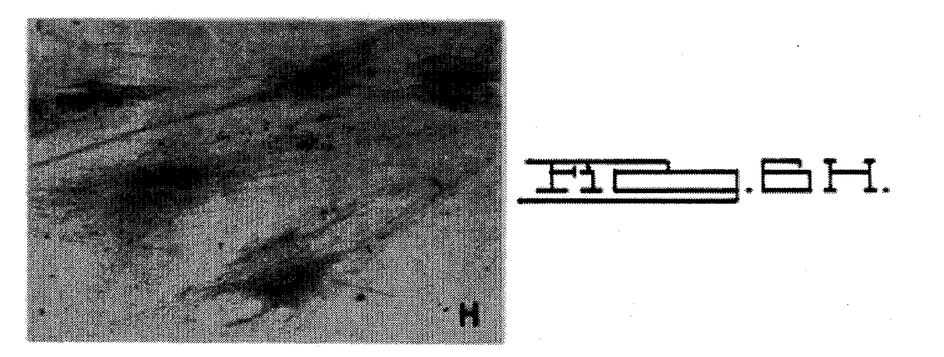

After attaching to the gelatin matrix, cells spread out with numerous cytoplasmic extensions extending from the cells. Within two weeks of plating, the cells had sufficiently spread to reach confluence as shown in the photomicrograph of Figure 4. "Splitting" the cells with trypsin and transferring them to 60 mm dishes and then T-75 flasks resulted in similar spreading to reach confluence. Utilizing EMEM the maximum number of passages before deterioration of cells was seven. Using MCDB 107, the maximum number of passages dropped to three. All cultures went through at least one passage in EMEM. Cells placed initially in MCDB 107, regardless of their age, failed to attach and grow. The phase-contrast microscopic appearance of cells cultured in MCDB 107 was "bat-winged," as shown in FIG. 5, and was similar to cells described in human fetal atrial myocardial cell cultures. See Claycomb, W.C. et al., In Vitro Cell. Dev. Biol. 25:1114–1120 (1989).

Growth characteristics were correlated with the age of the patient and pathology associated with myocardial tissue and are shown in Table 1 below.

TABLE 1

| PATIENT | HISTORY | AGE | COMMENTS |
|---|---|---|---|
| 1 | AVR, no CAD | 60 | Very few cells attached<br>Minimal growth |
| 2 | CAD, CABG × 3<br>Previous MI | 69 | No growth |
| 3 | AVR, no CAD | 55 | Little adherence<br>(10 cells)<br>Dead by 21 days |
| 4 | CABG, CAD | 40 | 3 passages EMEM |
| 5 | CABG, CAD | 44 | 7 passages EMEM<br>3 passages MCDB-107 |
| 6 | CABG, CAD | 56 | 3 passages EMEM |
| 7 | CABG × 3, HTN<br>CAD | 81 | No growth |
| 8 | CABG, CAD | 61 | No growth |
| 9 | CABG, CAD | 50 | Very few cells adhered<br>No growth |
| 10 | CABG, CAD | 38 | Excellent growth<br>1 passage EMEM<br>5 passages MCDB-107 |
| 11 | CABG, CAD | 41 | Excellent growth<br>1 passage EMEM<br>5 passages MCDB-107 |

KEY: AVR — Aortic valve replacement; CAD — Coronary artery disease; CABG — Coronary artery bypass graft; CABG × 3 — Triple bypass; HTN — Hypertension.

appears to have increased growth potential relative to older patient myocardial tissue, with some overlap.

Figure 7:
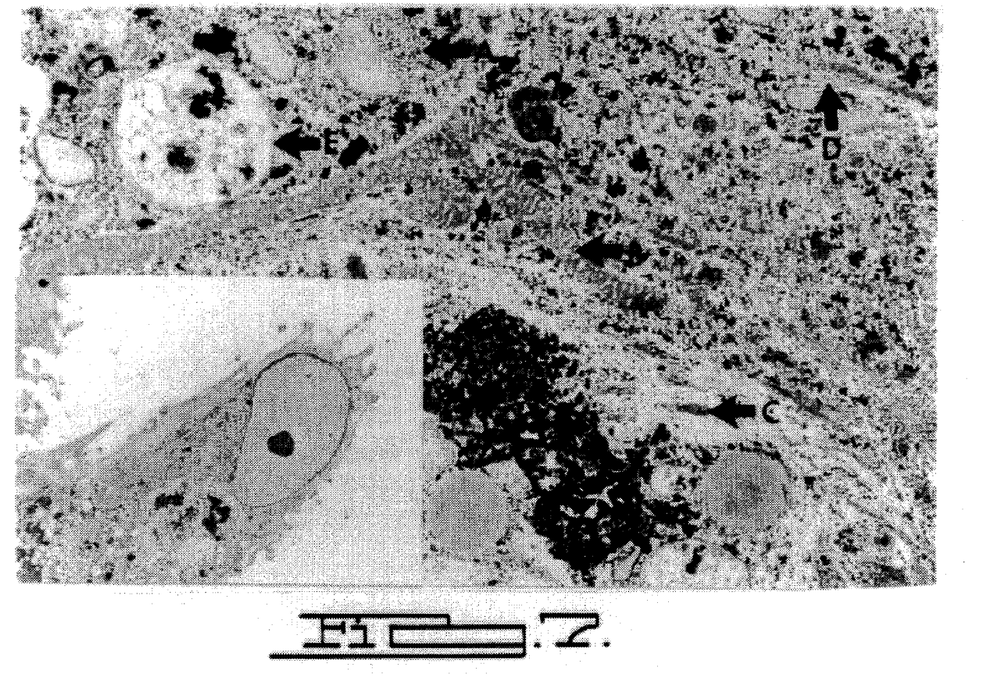
FIG. 7 is an electron photomicrograph (×16,300) of presumptive myocardiocytes cultured in MCDB 107: A) free ribosomes; B) pleomorphic mitochondria; C) dense Z-body with attached myofibrils; D) myofibrils; and E) autophagosome.

Characterization Monoclonal antibody immunoperoxidase stains were performed on presumptive myocardiocytes using fibroblasts and endothelial cells as controls. The stains showed characteristic staining of harvested cells for the proteins actin, myosin, myoglobin and atrial natruiretic factor while control cells did not. Factor VIII stains of endothelial cells highlighted their characteristic cytoplasmic granules while the same stains revealed no such granules in the presumptive myocardiocytes. As shown in FIG. 6, actin stains in the presumptive myocardiocytes demonstrated numerous cytoplasmic filaments while myosin and myoglobin stains showed more diffuse cytoplasmic staining. ANP showed definitive perinuclear staining. Electron microscopy of the presumptive myocardiocytes revealed that they were secretory cells containing numerous free ribosomes, rough endoplasmic reticulum and secretory granules. The cells also contained numerous microfilaments. No well organized sarcomeres or T-tubules were seen. However, as shown in FIG. 7, dense Z-bodies containing attached microfilaments, and pleomorphic mitochondria were prominent. The electron photomicrographic appearance is similar to that seen in adult rat myocardiocyte cultures at 14 days undergoing myofibrillar reorganization. Nakajima, T. et al., *Cir. Res.* 64(2):297–303 (1989).

SPECIFIC EXAMPLE 2.

Explant Method

MATERIALS AND METHODS

Atrial tissue was obtained fresh from patients undergoing cardiovascular procedures requiring cardiopulmonary bypass. The right atrial appendage was removed to insert the venous bypass cannula. The appendage was placed immediately in cold Hank's Balanced Salt Solution (HBSS) without calcium or magnesium (Whittaker, Walkerville, Mass.). The tough epicardial layer was stripped from the appendage using sharp dissection. The remaining pure myocardial muscle was minced into small (0.5–1.0 mm$^3$) pieces and rinsed in cold HBSS. The minced atrial tissue was partially digested in collagenase solution containing 25 cc HBSS; 10 cc Eagle's Minimal Essential Medium (EMEM) with Earle's Salts (Whittaker) containing 30% newborn calf serum (Whittaker) and 0.1% antibiotic solution (Gibco-10,000 units/cc Penicillin G, 10,000 µg/cc Streptomycin and 25 µg/cc Amphotericin B); and collagenase (Worthington, Freehold, N.J.) 1.43 mg/ml. After two hours of digestion in a shaker at 37° C. at 125 rpm, the pieces were removed and placed in 35 mm dishes (Corning, Corning, N.Y.). All culture dishes were coated with 0.2% gelatin (Difco, Detroit, Mich.) and incubated overnight at 5° C. prior to use. The explants were cultured in 2.2 cc EMEM at 37° C. and 5% $CO_2$. They were allowed to attach to the gelatin matrix. After attachment, the culture medium was changed every 3–5 days.

Cell Separation

Cells which spread out from the explant were separated using selective attachment techniques. The cultures were split with 0.62% trypsin using standard laboratory techniques and the resulting cell suspension plated on fresh 60 mm dishes (Corning). Cells which did not attach after 30 minutes were removed and discarded. The remaining adherent cells were cultured in MCDB 107 (Sigma, Saint Louis, Mo.). The culture media was changed every 3–5 days.

Cell Characterization

The separated fraction of cells was split using trypsin and plated on 24 well plates (Corning) at 1×10$^5$ cells/cc. The cultures were allowed to grow to 40–50% confluence in MCDB 107, then fixed with 5:95 acid-ethanol fixative. They were characterized with immunoperoxidase stains for smooth muscle α-actin (Lipshaw, Detroit, Mich.), myoglobin (Dako, Carpinteria, Calif.) and atrial natriuretic polypeptide (ANP) (Research and Diagnostic Antibodies, Berkeley, Calif.). The antibodies were used with Immunon/Lipshaw's OmniTag Avidin Biotin Affinity Immunoperoxidase System using the procedures provided with the kits (Lipshaw). A portion of the separated fraction of cells were fixed with 2.5% glutaraldehyde/0.2M cocodylate buffer (Polysciences, Inc., Warrington, Pa.) at a pH of 7.4, postfixed with 1% osmium tetraoxide (Polysciences, Inc.) embedded in Epon LX-112 resin (Ladd's Research, Burlington, Va.), stained with 0.03% lead citrate (Eastman Kodak, Rochester, N.Y.) and saturated uranyl acetate in 50% ethyl alcohol (Pelco, Co., Tustin, Calif.), and examined using transmission electron microscopy. Several pieces of fresh explanted myocardium were fixed, stained and examined in the same fashion for comparison.

Cell Proliferation Assay

A portion of the separated fraction of cells plated on the 24 well plates was allowed to grow to 40–50% confluence. 5-Bromo-2'-deoxyuridine (BrdU) was added to the culture medium (1:100 dilution of the labeling reagent provided in the Amersham Cell Proliferation Kit) and the cells incubated for 46 hours. The cells were fixed in 5:95 acid-ethanol fixative and stained with an immunoperoxidase stain for BrdU per instructions provided in the cell proliferation kit (Amersham, Amersham, UK). The cells with myocardial morphology which stained positive for BrdU were counted. Planimetric cell counts of the entire population of cells were performed daily at four standard locations on the plate for ten days, concluding at the time of BrdU incorporation. The increase in cell counts was calculated. The number of cells replicating their DNA (staining positive for BrdU) was divided by the total number of cells on the plate and the result was multiplied by 100. This number represented the percentage of cells undergoing mitosis for a given period of time and was labeled the mitotic index.

RESULTS

Figure 9:
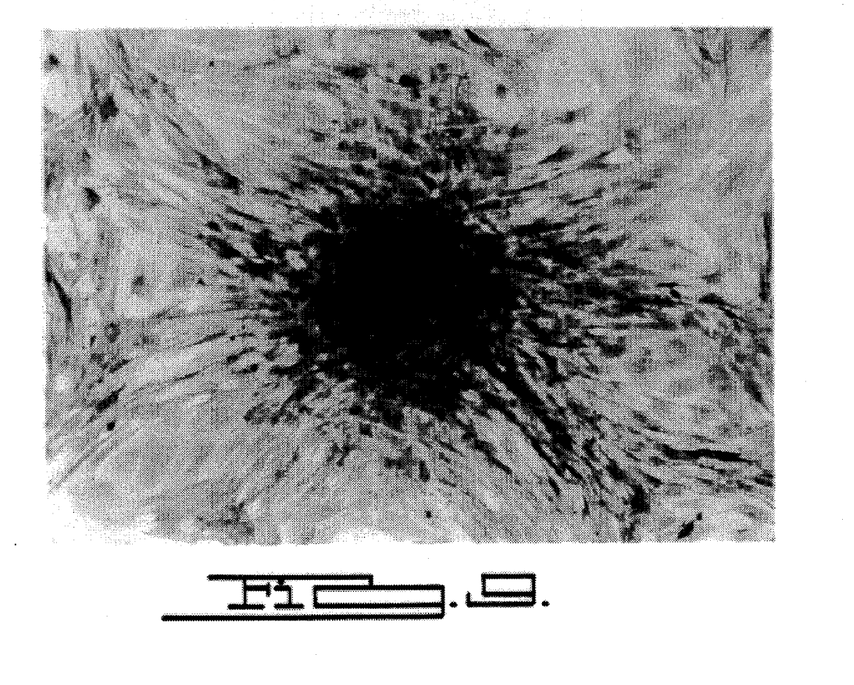
FIG. 9 is a light photomicrograph (×50) of explanted human adult atrial myocardium and migrating cells stained with anti-α smooth muscle actin.
Figure 10:
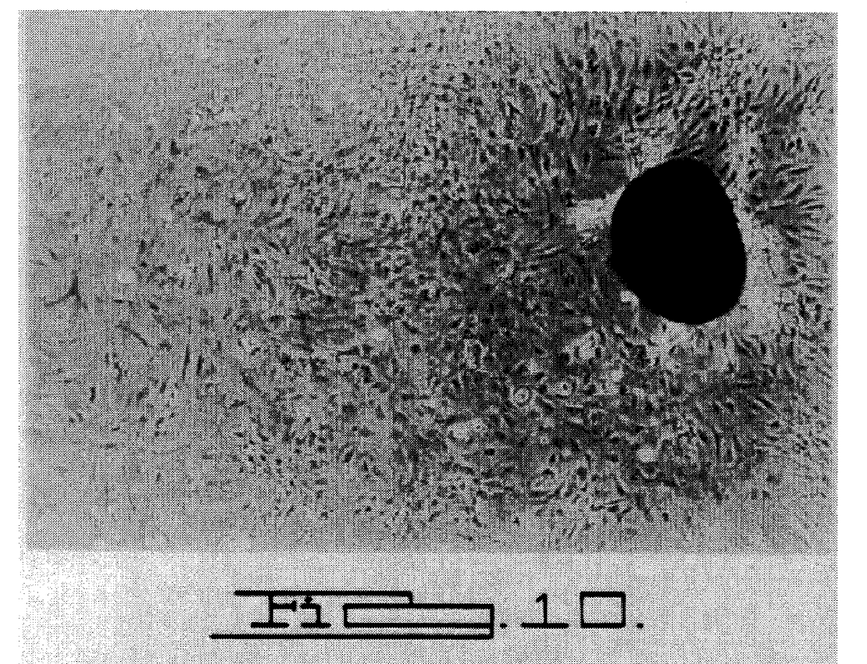
FIG. 10 is a phase-contrast photomicrograph (×50) of explanted human adult atrial myocardium with cells migrating from it.

The minced atrial tissue quickly settled to the bottom of the culture plates. The pieces became adherent to the gelatin matrix after 5–7 days. Soon after the explants became adherent, cells began to migrate from them. As shown in FIG. 9, actin stains performed on actively migrating cultures demonstrate numerous large cells coming off which possessed actin filaments and myocardial cell morphology. The resulting culture of cells, derived solely from the explants, contained a mixture of cell types. Phase-contrast microscopy demonstrated a variety of cell sizes and morphologies as shown in FIG. 10. When this mixed culture was split and plated at low density, individual cell types could be identified.

Figure 11:
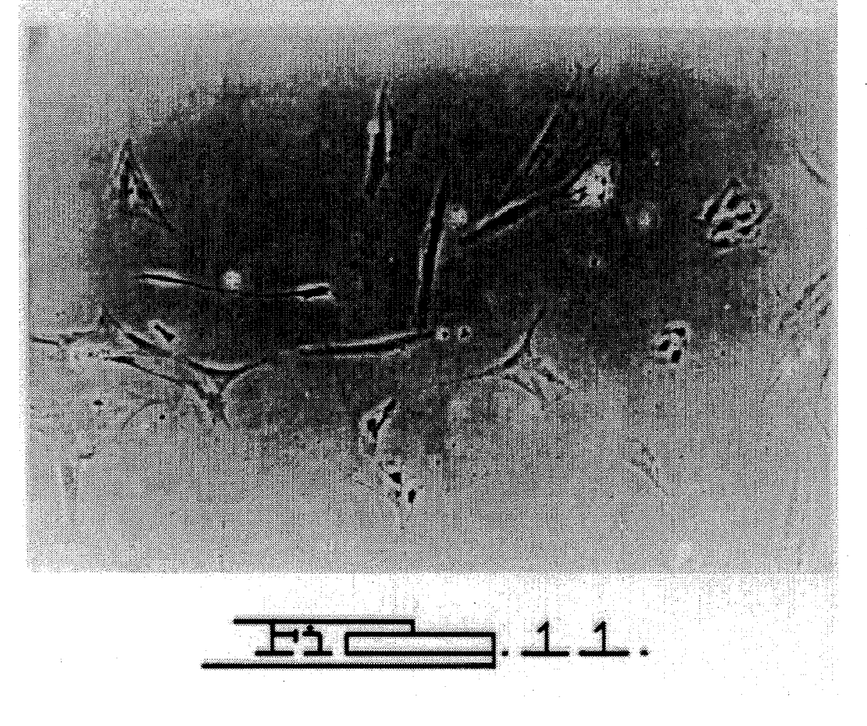
FIG. 11 is a phase-contrast photomicrograph (×125) of a mixed culture of cells obtained from explanted human adult atrial myocardium plated at low density.
Figure 12:
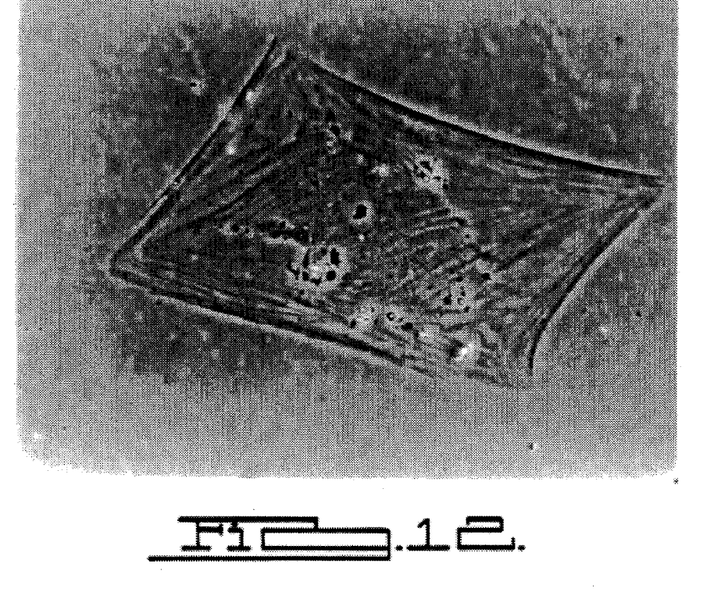
FIG. 12 is a phase-contrast photomicrograph (×500) of isolated human adult atrial myocytes demonstrating prominent cytoplasmic myofilaments.
Figure 13:
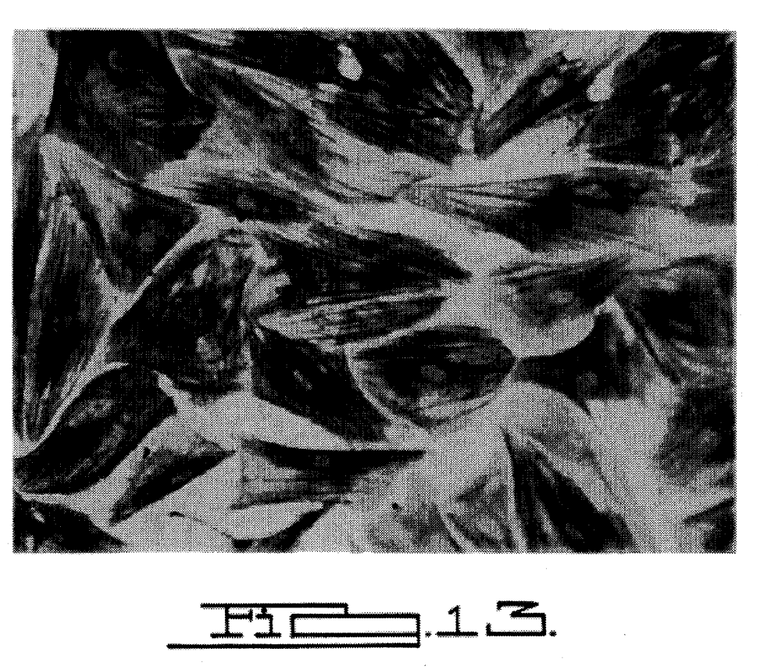
FIG. 13 is a light photomicrograph (×250) of cultured human adult atrial myocytes stained with anti-α smooth muscle actin immunoperoxidase stain.
Figure 14:
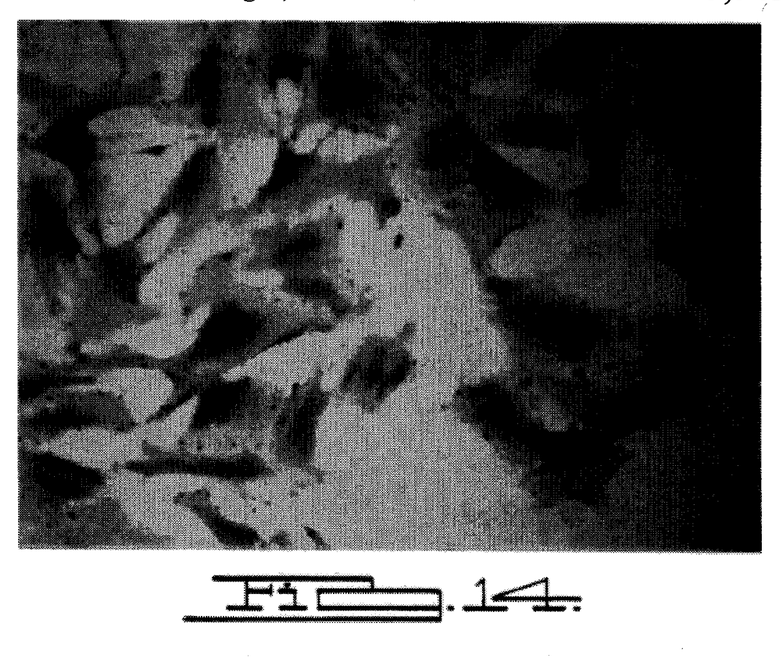
FIG. 14 is a light photomicrograph (×250) of cultured human adult atrial myocytes stained with anti-myoglobin immunoperoxidase stain.
Figure 15A:
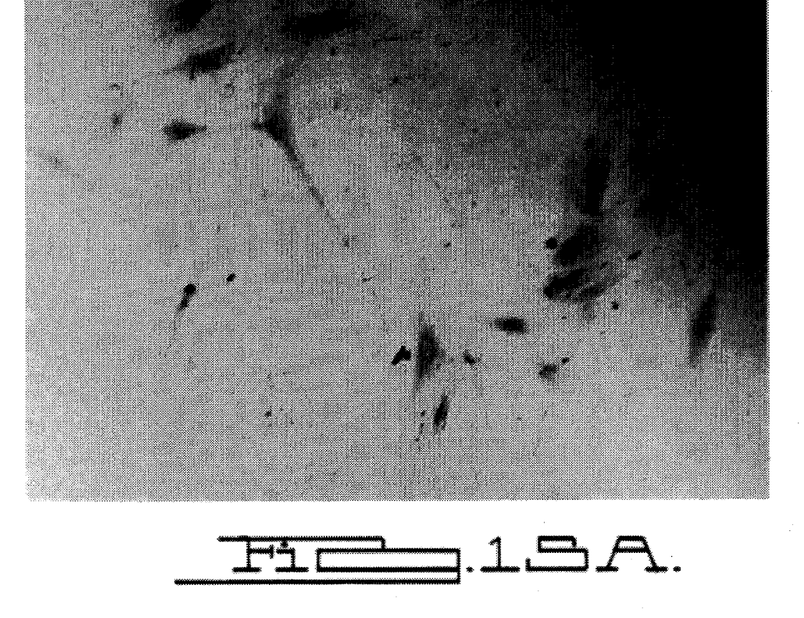
FIGS. 15A and 15B are light photomicrographs (×50) of A) cultured human adult atrial myocytes with perinuclear granules stained with anti-Atrial Natriuretic Polypeptide (ANP) immunoperoxidase stain; and B) identical control culture stained without primary anti-ANP antibody.
Figure 15B:
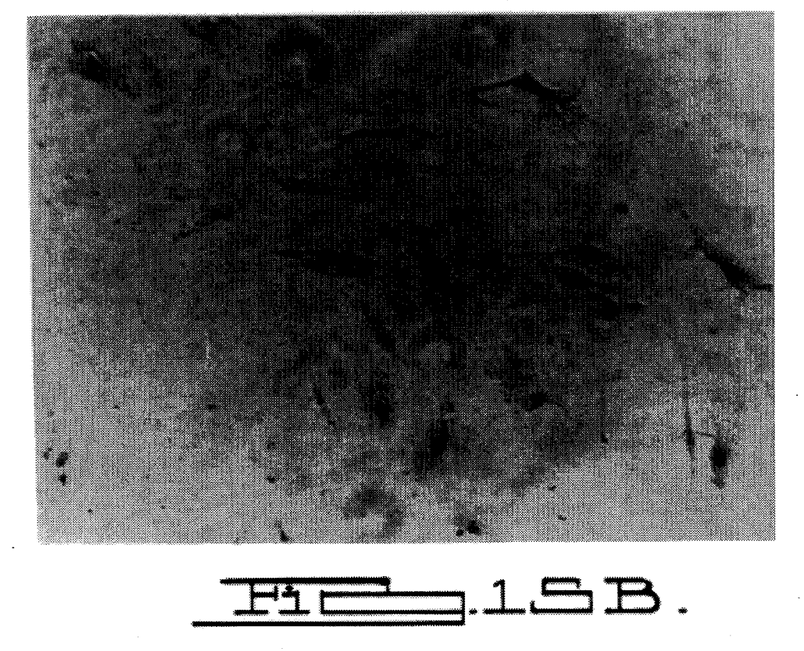

As shown in the phase-contrast photomicrograph of FIG. 11, four main cell morphologies emerged. -One fraction could be separated from the rest using the selective attachment techniques described above. This fraction, on phase-contrast microscopy, depicted in FIG. 12, possessed large cells which measured an average of 200×80 microns, were polygonal or "bat-winged" in shape, possessed prominent cytoplasmic filaments oriented longitudinally along the axis of the cell and displayed contact inhibition not overlapping their cytoplasm. Immunoperoxidase staining showed the cytoplasmic filaments to be composed of actin. The cytoplasm also diffusely stained positive for actin as shown in FIG. 13, and myoglobin as shown in FIG. 14. As shown in FIG. 15, perinuclear granules were present which stained intensely for atrial natriuretic polypeptide. Quantitative counts of actinstained cultures revealed this separated fraction of cells to be 93% myocardiocytes.

Figure 16:
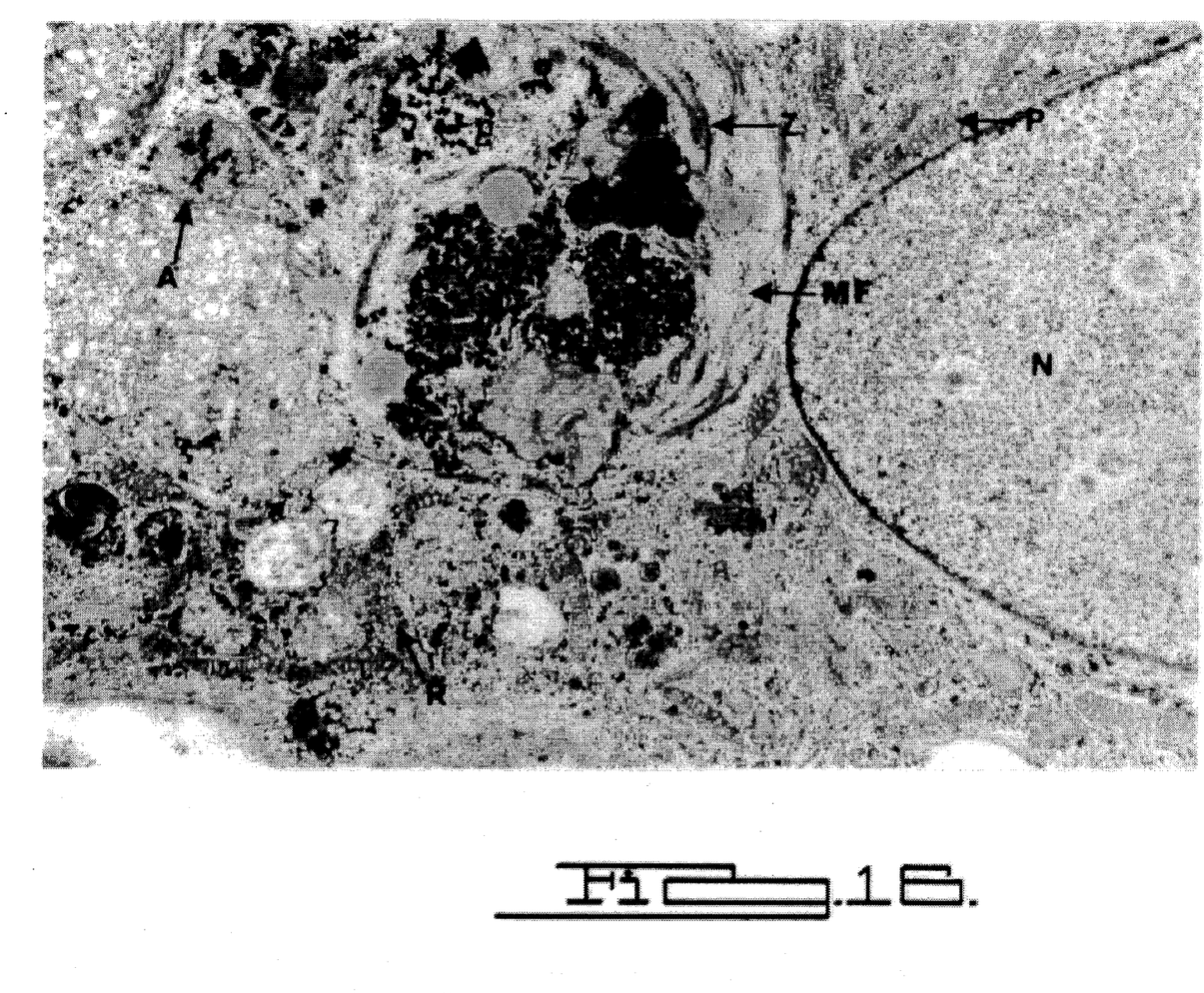
FIG. 16 is a transmission electron photomicrograph (×10,500) of cultured human adult atrial myocyte: A) autophagosome; M) myofibrils; Z) Z-bodies; P) pleomorphic mitochondrium; R) rough endoplasmic reticulum and free ribosomes; and N) nucleus.
Figure 17:
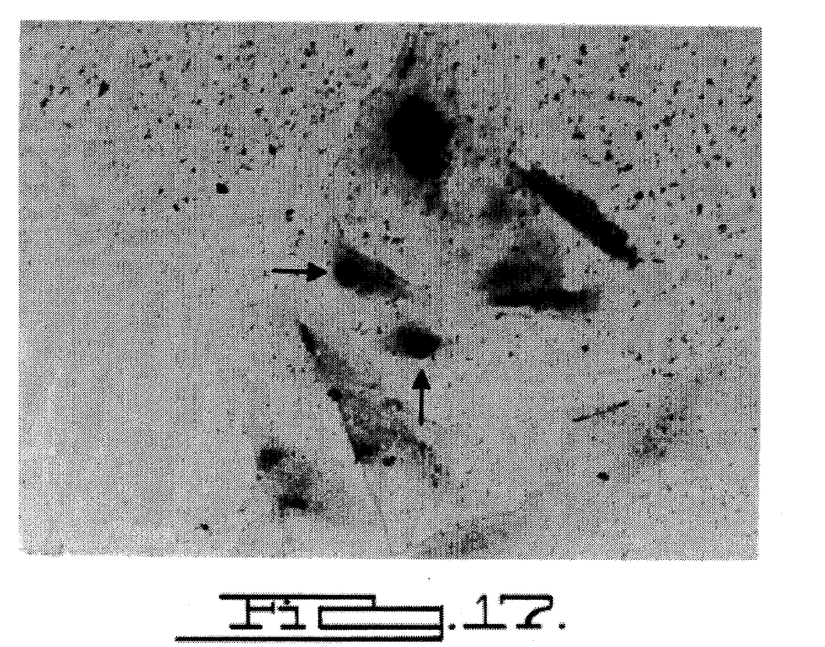
FIG. 17 shows bromo-deoxyuridine (BrdU) incorporated into DNA stained with anti-BrdU immunoperoxidase stain. Arrows indicate positively stained nuclei (×125).

Transmission electron microscopy, as shown in the photomicrograph of FIG. 16, revealed numerous bundles of myofibrils with interspersed dense Z-bodies, pleomorphic mitochondria, secretory granules and autophagosomes. No organized sarcomeres were present. In contrast, the electron photomicrographic appearance of fresh explanted tissue showed organized sarcomeres, round or ovoid mitochondria, sparse sarcoplasmic reticulum, but numerous free ribosomes. Planimetric cell counts over the ten day period prior to BrdU incorporation increased from 862±88 to 1010±100 for a 16% increase (p<0.03). Bromo-deoxyuridine incorporation over 48 hours and immunoperoxidase staining of the BrdU, shown in FIG. 17, demonstrated that 0.15% of cells with myocardial morphology were undergoing DNA replication for each 24 hour period.

The present invention provides for the isolation of human myocardial cells and methods for their culture. The methods and cultures of the present invention provide an extremely valuable research and diagnostic tool for studies of adult heart cell response to growth factors with respect to proliferation and differentiation. Cultures of the present invention can also be used to determine the effect of age or disease states on mitotic potential, for metabolic research or for a myriad of other studies which will be readily apparent to those skilled in the art.

The methods and cultures of the present invention can also be used to evaluate pharmaceutical agents for their ability to promote the growth, survival, or functional activity (e.g. contractility) of myocardium. Alternatively, such methods and cultures may be used to evaluate agents for the capability of inducing deleterious effects in myocardium. Putative therapeutic or, alternatively, toxic agents may be administered in serial dilutions to multiple myocardial cultures produced by the method of the invention, and the $ED_{50}$ or $TD_{50}$ may be calculated using standard techniques.

In further embodiments, myocardial cells may be extracted from patients who are suffering from cardiac disorders and cultured to monitor the success and direct the course of treatment. For example, patient myocardial cells can be evaluated for mitotic potential in response to various agents such as growth factors and pharmaceutical agents to determine if their administration would be beneficial to the patient. The methods of the present invention can also be used for the expansion of myocardial cells in culture for implantation in diseased or infarcted myocardium or in aneurysm repair. In further specific embodiments, atrial myocardial cells cultured by the methods of the invention may be used in vivo or in vitro as a source of atrial natriuretic peptide. For example, a cellular implant comprising such cells may be introduced into a patient as a source of atrial natriuretic peptide subject to biofeedback mechanisms.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

The various publications cited herein are hereby incorporated by reference in their entirety.

What is claimed is:

1. A method of reproducing human atrial mycocardiocytes in culture comprising the steps of:

providing a sample of human tissue comprising adult atrail cells;

growing at least a portion of the cells in the samples in culture medium to obtain a cell culture;

selecting for myocardinocytes in the culture; and maintaining the selected myocardiocytes in culture for a time sufficient and under culture conditions which allow for cell division of the myocardiocytes.

2. The method of claim 1, further comprising the step of partial dissociation of the cells in the tissue sample, wherein after the step of partial dissociation the sample comprises an explant tissue portion and a diassociated cell portion, and wherein the explant tissue portion comprises the portion grown in culture medium.

3. The method of claim 2, wherein after the step of dissociation the sample comprises substantially dissociated cells and the portion grown in culture medium comprises substantially dissociated cells.

4. The method of claim 3, wherein the step of selecting comprises growth of the substantially dissociated cells in growth medium selective for myocardiocyte growth.

5. The myocardiocyte culture produced by the method of claim 4.

6. The method of claim 2, wherein the explant tissue portion is cultured on a cell attachment matrix under conditions favorable for explant attachment, cell proliferation and migration from the explant tissue portion.

7. The method of claim 6, further comprising the step of isolating cells migrating from the explant tissue portion, wherein the isolated cells include myocardiocytes, and wherein the step of selecting further comprises the steps of placing the isolated cells on a cell attachment matrix for a time period sufficient for isolated myocardiocytes to attach to the matrix and removing unattached cells after the expiration of the time period.

8. The myocardinocyte culture produced by the method of claim 7.

9. The method of claim 7, wherein the step of selecting further comprises growth of the cells selected by attachment in growth medium selective for myocardiocyte growth.

10. The myocardiocyte culture produced by the method of claim 9.

11. The method of claim 1, wherein the step of maintaining the myocardiocytes in culture further comprises the step of growing the selected myocardiocytes to confluence in culture and passing the confluent myocardiocytes.

12. The myocardiocyte culture produced by the method of claim 1.

13. A method of reproducing human atrail myocardinocytes in culture comprising the steps of:

providing a sample of human atrail tissue comprising an explant tissue portion further comprising adult cells;

growing the explant tissue portion in culture medium to obtain a cell culture;

isolating cells migrating from explant tissue portion wherein the cells isolated include myocardiocytes;

plating the isolated cells on a cell attachment matrix;

selecting for myocardiocytes wherein the step of selecting further comprises the steps of maintaining the isolated cells in the cell attachment matrix for a time period sufficient for at least a portion of myocardiocytes present in the isolated cells to attach to the matrix and removing unattached cells after expiration of the time period; and maintaining the selected myocardiocytes in culture for a time sufficient for cell division to occur.

14. The method of claim 13, further comprising the step of dissociating a portion of the cells of the sample to provide the explant tissue portion and a dissociated cell portion.

15. The method of claim 14, wherein the step of dissociation further comprises partial dissociation of the sample through enzymatic digestion of the tissue sample.

16. The method of claim 13, wherein the time period is approximately 30 minutes.

17. The myocardinocyte culture produced by the method of claim 13.

18. A method of reproduce human atrial myocardiocytes in culture comprising the steps of:
- providing a sample of adult human atrail tissue;
- substantially dissociating the cells in the samples;
- growing the dissociated cells in culture medium to provide a cell culture;
- selecting for myocardiocytes in at least a portion of the disassociated cells; and
- growing the selected myocardiocytes in culture for a time sufficient to allow cell division to occur in at least a portion of the myocardiocytes.

19. The method of claim 18, wherein the step of substantial dissociation further comprises sequential digestion by an enzyme for a time period in the range of approximately two to nine hours.

20. The method of claim 19, wherein the enzyme used for digestion is collagenase and the time period of digestion is in the range of approximately six to seven hours.

21. The method of claim 18, wherein the step of selecting comprises culturing the dissociated cells in growth medium selective for myocardiocyte growth.

22. The myocardiocyte culture produced by the method of claim 21.

23. The myocardinocyte culture produced by the method of claim 18.

* * * * *